US011278688B2

(12) United States Patent
Azevedo

(10) Patent No.: US 11,278,688 B2
(45) Date of Patent: Mar. 22, 2022

(54) INHALING DEVICE FOR HEAVY METAL SALTS AND A METHOD OF USE THEREOF FOR MEDICAL TREATMENT

(71) Applicant: Max Azevedo, Lenoir, NC (US)

(72) Inventor: Max Azevedo, Lenoir, NC (US)

(*) Notice: Subject to any disclaimer, the term of this patent is extended or adjusted under 35 U.S.C. 154(b) by 0 days.

(21) Appl. No.: 17/060,405

(22) Filed: Oct. 1, 2020

(65) Prior Publication Data

US 2021/0283351 A1 Sep. 16, 2021

Related U.S. Application Data

(60) Provisional application No. 62/988,836, filed on Mar. 12, 2020.

(51) Int. Cl.

| | |
|---|---|
| ***A61M 15/06*** | (2006.01) |
| ***A61K 33/30*** | (2006.01) |
| ***A61K 9/00*** | (2006.01) |
| ***A61M 11/04*** | (2006.01) |
| ***A61M 15/00*** | (2006.01) |
| *A61K 47/10* | (2017.01) |

(52) U.S. Cl.

CPC ........... *A61M 15/06* (2013.01); *A61K 9/0078* (2013.01); *A61K 33/30* (2013.01); *A61M 11/042* (2014.02); *A61M 15/0021* (2014.02); *A61K 47/10* (2013.01); *A61M 15/0028* (2013.01); *A61M 2205/36* (2013.01); *A61M 2205/8206* (2013.01)

(58) Field of Classification Search

CPC .............. A61M 15/06; A61M 15/0021; A61M 2205/36; A61M 2205/8206; A61K 9/0078; A61K 33/30

See application file for complete search history.

(56) References Cited

U.S. PATENT DOCUMENTS

| | | | | |
|---|---|---|---|---|
| 6,017,901 A * | 1/2000 | Khan | A61K 47/61 | 424/1.73 |
| 2001/0032647 A1* | 10/2001 | Schuster | A61M 15/0045 | 128/204.17 |
| 2006/0102175 A1* | 5/2006 | Nelson | A61M 11/042 | 128/200.24 |
| 2007/0045288 A1* | 3/2007 | Nelson | A61M 15/008 | 219/533 |

(Continued)

FOREIGN PATENT DOCUMENTS

| | | |
|---|---|---|
| DE | 102017003667 A1 | 10/2018 |
| WO | 2019046510 A1 | 3/2019 |

*Primary Examiner* — Tu A Vo

(74) *Attorney, Agent, or Firm* — Boudwin Intellectual Property; Daniel Boudwin

(57) ABSTRACT

An inhaling device for heavy metal salts and a method of use thereof for medical treatment is provided. The device has a housing defining an interior volume. A mouthpiece is disposed at a terminal end of the housing. A slot is also disposed in the housing, wherein the slot is configured to receive a removably securable cartridge. The cartridge includes at least one heavy metal salt in a solution. Upon securement of the cartridge into the housing, the mouthpiece is in fluid communication with the solution. A battery powered heating element is disposed in the interior volume of the housing, wherein the heating element is in thermal communication with the cartridge when the cartridge is secured within the housing. In use, a user can heat the solution via the heating element and inhale the solution via the mouthpiece.

17 Claims, 2 Drawing Sheets

(56) References Cited

U.S. PATENT DOCUMENTS

| | | | | |
|---|---|---|---|---|
| 2007/0283972 | A1* | 12/2007 | Monsees | A24F 40/48 131/273 |
| 2008/0066741 | A1* | 3/2008 | LeMahieu | A61M 15/00 128/200.21 |
| 2008/0268060 | A1* | 10/2008 | Nguyen | A61M 11/041 424/489 |
| 2009/0151717 | A1* | 6/2009 | Bowen | A61M 11/048 128/200.23 |
| 2009/0180968 | A1* | 7/2009 | Hale | A61M 11/042 424/40 |
| 2010/0242976 | A1* | 9/2010 | Katayama | A24B 15/16 131/273 |
| 2011/0226236 | A1* | 9/2011 | Buchberger | A24F 40/46 128/200.23 |
| 2012/0082720 | A1* | 4/2012 | Ang | A61P 31/22 424/463 |
| 2013/0042865 | A1* | 2/2013 | Monsees | A24F 1/32 128/203.27 |
| 2013/0239956 | A1* | 9/2013 | Schulz | B05B 17/0646 128/200.14 |
| 2014/0263721 | A1* | 9/2014 | Schulz | A61M 15/00 239/102.1 |
| 2014/0377373 | A1 | 12/2014 | Mullin et al. | |
| 2015/0027440 | A1* | 1/2015 | Schuschnig | A61M 11/005 128/200.14 |
| 2015/0224077 | A1* | 8/2015 | Gerhart | A61K 31/4741 514/456 |
| 2015/0238712 | A1* | 8/2015 | Gallem | A61M 15/0028 128/200.23 |
| 2016/0295919 | A1* | 10/2016 | Thomas, Jr. | A24F 40/42 |
| 2016/0309789 | A1* | 10/2016 | Thomas, Jr. | A24F 40/485 |
| 2016/0338412 | A1* | 11/2016 | Monsees | A61M 11/042 |
| 2016/0345630 | A1* | 12/2016 | Mironov | B32B 3/266 |
| 2016/0353801 | A1* | 12/2016 | Zinovik | A24F 40/42 |
| 2016/0353802 | A1* | 12/2016 | Malgat | A24F 40/70 |
| 2017/0021026 | A1* | 1/2017 | Naheed | A61K 47/44 |
| 2017/0368282 | A1* | 12/2017 | Knoch | A61M 16/0003 |
| 2018/0027884 | A1* | 2/2018 | Zuber | A61M 15/06 |
| 2018/0042304 | A1* | 2/2018 | Hogwood | A24F 40/46 |
| 2018/0104425 | A1* | 4/2018 | Hogwood | A24F 40/42 |
| 2018/0146711 | A1* | 5/2018 | Mazur | A61M 11/042 |
| 2018/0168231 | A1* | 6/2018 | Reevell | A61M 11/042 |
| 2018/0289909 | A1* | 10/2018 | Lindars | A61M 15/06 |
| 2019/0098930 | A1* | 4/2019 | Fallon | A24F 40/42 |
| 2019/0099566 | A1* | 4/2019 | Gramann | A61M 15/02 |
| 2019/0254345 | A1* | 8/2019 | Hepworth | A61M 15/06 |
| 2019/0254346 | A1* | 8/2019 | Hepworth | A61M 15/0028 |
| 2019/0289916 | A1* | 9/2019 | Bowen | F21V 33/0004 |
| 2019/0314586 | A1* | 10/2019 | Minskoff | A61M 11/02 |
| 2020/0022416 | A1* | 1/2020 | Alarcon | G16H 40/63 |
| 2020/0068945 | A1* | 3/2020 | Banks | A24B 15/16 |
| 2020/0120989 | A1* | 4/2020 | Danek | A61K 31/465 |
| 2020/0230329 | A1* | 7/2020 | Danek | A24F 40/05 |
| 2020/0288780 | A1* | 9/2020 | Martin | A24F 13/00 |
| 2021/0127757 | A1* | 5/2021 | Lee | A61M 15/06 |
| 2021/0145050 | A1* | 5/2021 | Ricketts | A61M 11/042 |

* cited by examiner

INHALING DEVICE FOR HEAVY METAL SALTS AND A METHOD OF USE THEREOF FOR MEDICAL TREATMENT

CROSS REFERENCE TO RELATED APPLICATIONS

This application claims the benefit of U.S. Provisional Application No. 62/988,836 filed on Mar. 12, 2020. The above identified patent application is herein incorporated by reference in its entirety to provide continuity of disclosure.

BACKGROUND OF THE INVENTION

The present invention relates to medical treatments. More particularly, the present invention provides for a device that can be used in conjunction with a solution containing at least one heavy metal salt, wherein the solution can be aerosolized and inhaled as a method of treatment for various ailments, diseases, and the like.

Many people utilize injections to administer drugs and medications directly into a patient's blood system in order to treat bacterial or viral infections as well as other medical conditions. Other forms of administration include ingestion or suppository use in order to introduce the medication to the patient's system. Presenting medications via these methodologies leads to a tortuous pathway through the digestive system, or similar systems. Such methodologies can have significant lag time to efficacy. The "shotgun" approach taken by these methods delivers the treatment to the entire body, which, in turn, follows transmission across body tissue to reach the attacking microbe or site of treatment. Because the approach taken delivers treatment to the entire body, the concentrations of the medications and drugs much be sufficiently high in order to enable an adequate amount of medication to reach the targeted area.

In some instances, inhalation of medication is offered as an alternate pathway to introduce the desired drug to a patient's system. Respirators and inhalators are well known in the art but do not utilize soluble salts and rely on depositing the medications on fine particles. These fine particles act as carriers to transport the medication into the lungs and related circulatory pathways. For example, cyanoacrylate polymer microparticles can be used as such a transporter, resulting in the patient inhaling dust, in effect. Such transporters can damage a patient's system and necessitate a larger volume of material needed to be inhaled in order to provide sufficient quantities of the desired medication.

Inhalation devices, such as respirators, tend to heat the desired material in order to vaporize it. Some devices utilize pressure with or without heat in order to properly aerosolize the desired molecules. There are numerous other ways, such as humidifiers, that are used to generate aerosols by heat or electronically via ultrasonic waves. All of these such inhalant devises deliver nano sized, or comparably sized particles and some are propelled by fluorinated hydrocarbons, or other pressurizing agents.

The present invention substantially diverges in design elements from the known art and consequently it is clear that there is a need in the art for an improvement to existing medical treatment devices. In this regard the present invention substantially fulfills these needs.

SUMMARY OF THE INVENTION

In view of the foregoing disadvantages inherent in the known types of medical treatments now present in the art, the present invention provides for a device that can be used in conjunction with a solution containing at least one heavy metal salt, wherein the solution can be aerosolized and inhaled as a method of treatment for various ailments, diseases, and the like. The present inhaling device for heavy metal salts and a method of use thereof for medical treatment comprises a housing defining an interior volume. A mouthpiece is disposed at a terminal end of the housing. A slot is also disposed in the housing, wherein the slot is configured to receive a removably securable cartridge. The cartridge includes at least one heavy metal salt in a solution. Upon securement of the cartridge into the housing, the mouthpiece is in fluid communication with the solution. A battery powered heating element is disposed in the interior volume of the housing, wherein the heating element is in thermal communication with the cartridge when the cartridge is secured within the housing. In use, a user can heat the solution via the heating element and inhale the solution via the mouthpiece.

An object of the present invention is to provide an inhaling device for heavy metal salts that can be used to inhale a solution containing at least one heavy metal directly through a mouthpiece of the device.

Another object of the present invention is to provide a simple device contrasting the current bulky inhalation devices for respiration therapies that has the simplicity of charging disposable individual dose cartridges/ampules into the present device.

Another object of the present invention is to provide an inhaling device for heavy metal salts that includes a heating element, wherein the heating element can be used to aerosolize a solution containing at least one heavy metal salt such that the solution can be directly inhaled through a mouthpiece of the device.

Another object of the present invention is the creation of a solution containing at least one heavy metal salt, wherein the solution can be introduced to a reservoir of an electronic cigarette, the electronic cigarette can then be used to inhale the solution.

Another object of the present invention is the use of volatile solvents to deliver micron and sub-micron metal salts by vaporization from the metal salts. Particles of five (5) microns will travel to the smaller airways but those having lower than two (2) microns are able to settle in the alveolar region of the lung. A proper choice of the carrier solvent(s) will control the evaporation rate and thus the resultant size of the delivered particles.

Other objects, features, and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
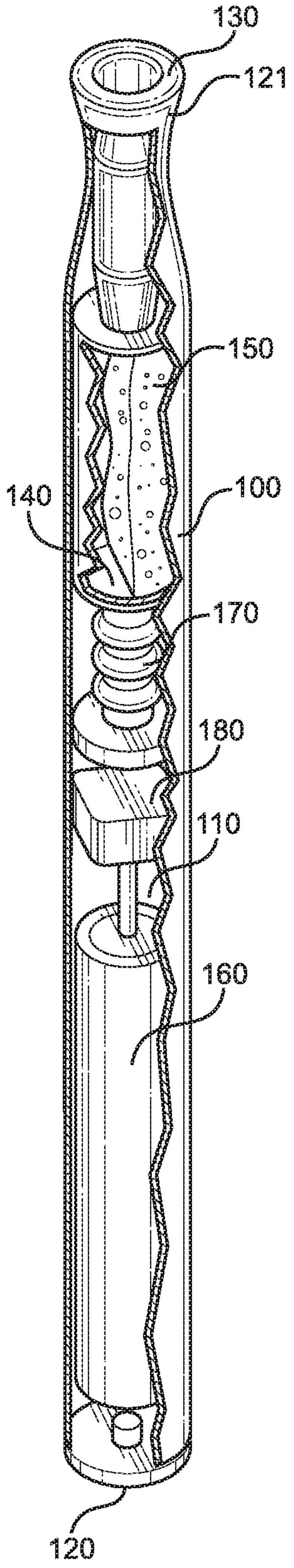
FIG. 1 shows a cut-away view of an inhaling device in an embodiment of the inhaling device for heavy metal salts.

Reference is made herein to the attached drawings. Like reference numerals are used throughout the drawings to depict like or similar elements of the inhaling device for heavy metal salts. For the purposes of presenting a brief and clear description of the present invention, a preferred embodiment will be discussed as used for the inhaling device for heavy metal salts. The figures are intended for representative purposes only and should not be considered to be limiting in any respect.

Although the characteristic features of this invention will be particularly pointed out in the claims, the invention itself and manner in which it may be made and used may be better understood upon review of the following detailed description.

For the purposes of presenting a brief and clear description of the present invention, the preferred embodiment will be discussed as used for administering a solution containing at least one heavy metal to a user by inhalation via the use of a mouthpiece of an inhaling device. The following detailed description is intended for representative purposes only and should not be considered limiting in any respect.

Figure 2:
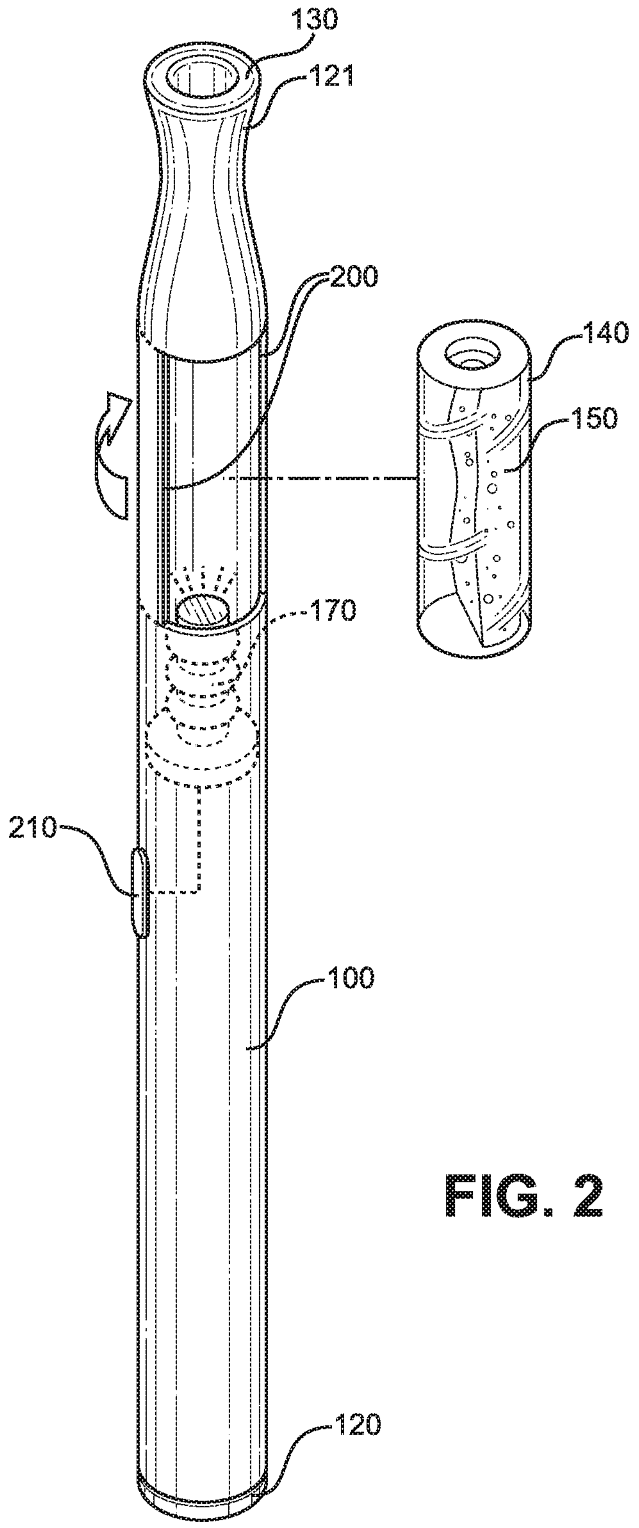
FIG. 2 shows an exploded view of an inhaling device in an embodiment of the inhaling device for heavy metal salts.

Referring now to FIGS. 1 and 2, there are shown a cut-away view of an inhaling device in an embodiment of the inhaling device for heavy metal salts and an exploded view of an inhaling device in an embodiment of the inhaling device for heavy metal salts. In one embodiment, the inhaling device for heavy metal salts has a housing 100 defining an interior volume 110. In the shown embodiment, the housing 100 is a tube that includes a closed end 120 and an open end 121. A mouthpiece 130 is disposed at the open end 121 of the housing 100 such that the mouthpiece 130 is in fluid communication with a cartridge 140 removably secured within the internal volume 110 (as shown in FIG. 2). One of ordinary skill in the art will understand that the housing 100 is utilized as an inhalation device and therefore can take a number of sizes and shapes in order to accommodate a user's design and aesthetic preference. For example, in various embodiments the housing 100 is an electronic cigarette with a reservoir that can receive a desired fluid to be "smoked" and therefore inhaled by the user.

In one embodiment, a slot 200 (as shown in FIG. 2) is disposed in the housing 100, wherein the slot 200 is configured to receive a removably securable cartridge 140. The cartridge 140 includes at least one heavy metal salt in a solution 150. One of ordinary skill in the art will understand that the cartridge 140 containing the heavy metal salt in solution 150 can be used as packaging and the cartridge 140 can be opened to enable a user to transfer the solution 150 from the cartridge 140 to a reservoir of a device such as an electronic cigarette. However, in various embodiments, the housing 100 is configured to receive the cartridge 140 and position the solution 150 therein in a desired orientation such that a user can inhale the solution 150 without opening the cartridge 140 prior to insertion. In such embodiments, upon securement of the cartridge 140 within the housing 100, the cartridge 140 and solution 150 are aligned in the housing 100 such that the mouthpiece 130 is in fluid communication with the solution 150. In this manner, a user will have access to the solution 150 and will be able to inhale the solution 150 via the mouthpiece 130 of the housing 100. In various embodiments, upon securement of the cartridge 140 into the housing 100, the solution 150 can be inhaled by simple air respiration utilizing the mouthpiece 130. In some such embodiments, the solution 150 is highly volatile and therefore is easily evaporated and changes to a gaseous phase at standard room temperature and pressure. In one embodiment, the inhaling device for heavy metal salts can be fitted to an air supply and thus provide an aerosolized treatment in proximity of the user enabling unassisted breathing without other devices. In other embodiments, the inhaling device for heavy metal salts, and the solution 150 in particular, can be fitted in-line for individuals who utilize various devices to assist their breathing.

In one embodiment, the housing 100 includes a battery 160 powered heating element 170 disposed in the interior volume 110 of the housing 100. The battery 160 powered heating element 170 is in thermal communication with the cartridge 140 and the solution 150 when the cartridge 140 is secured within the housing 100. In this manner, the heating element 170 can warm and heat the solution 150 in the cartridge 140 to assist in aerosolizing the solution 150. The aerosolized or misted solution 150 can then be inhaled by a user as a therapeutic treatment. In some embodiments, the battery 160 powered heating element 170 is in communication with a controller 180, wherein the controller 180 can adjust the amount of heat provided. In the embodiment shown in FIG. 2, a button 210 is in communication with the controller 180, wherein the button 210 can selectively actuate the heating element 170 such that the user can control when the heating element 170 provides heat.

The inhaling device for heavy metal salts can be used in conjunction with various therapeutic remedies in the form of a solution. In one embodiment, the heavy metal salt in the solution is a zinc compound. One of ordinary skill in the art will understand that the activity of zinc as an effective reducer of cold symptoms has been clinically established and some existing medications utilize zinc for such a treatment. However, these treatments are not provided in an aerosolized form and have limited reach to migrate to the periphery of the respiratory system. Devices in the present art do not utilize soluble salts, as provided by the present invention. Instead, devices in the present art use solid materials impregnated with the active pharmaceutical and are propelled by fluorinated hydrocarbons. The present invention avoids the unnecessary introduction of the solid materials and the fluorinated hydrocarbons when aerosolizing and introducing the solution to the user's respiratory system, thereby eliminating the introduction of such unnecessary, and potentially harmful, chemicals and materials.

It is noted that comparable compositions are presented in US Patent Application number 2014/0377373 (hereinafter the "'7373 Disclosure") which describes microbial intervention with zinc compounds at epithelial cell walls. The cited reference is incorporated herein as an added explanation of the protective mechanism of zinc compounds. Further, in particular regards to viruses, are numerous publications and studies describing the inhibitory activity preventing virus replication. The apparent strength of zinc compounds is therefore twofold in that the epithelial cell is more resilient to viral attack and if compromised, the replication inhibition provides another barrier. The '7373 Disclosure relies on oral, colorectal, bladder, uterine, nasal, vaginal, penile, nasopharengial, buccal, intestinal epithelia, or mucosal routes of delivery. Notably absent from the '7373 Disclosure is a respiratory tract route of deliver. Further, the present device can be differentiated from the '7373 Disclosure's claim of prophylactic use within 1-3 hours of exposure. The delivery of these compositions via the present device to the respiratory tract can be both preventative as well as remedial.

In various embodiments, the solution includes co-diluents to aid in thinning the solution. Some therapeutic treatments involving heavy metal salts can be too viscous or too dense to easily flow from one point to another or may not be able to dissolve the heavy metal salts at all, thereby resulting in a suspension of the heavy metal salt. The inclusion of the co-diluents enables the solution to be thinned, and in some cases to dissolve the heavy metal salt into the solution. In some embodiments, the co-diluent is a water compatible organic. In some embodiments, the co-diluent can be propylene glycol, glycerine, butanediol, triethylene glycol, esters of poly hydric alcohols, and ethanol. Ethanol has favorable properties of low boiling point and resistance to degradation as a consequence of the volatility. In other embodiments, candidates for carriers and diluents include low boiling esters in ranges comparable to ethanol and combinations of such. Some examples include ethyl acetate, propyl and isopropyl acetate. The advantage of these very volatile compositions is the facile ability to atomize the formulations with minimal power load.

In one embodiment, the solution is a five-percent aqueous solution of zinc acetate. In a further embodiment, the five-percent aqueous solution of zinc acetate is diluted with propylene glycol to make a two percent concentration in glycol. In the preferred embodiment, the solution comprises zinc acetate dihydrate. In some formulations zinc oxide nanoparticles have been observed. Such zinc oxide nanoparticles may have undesirable health effects, and therefore there is a need for preventing their formation. In some embodiments, an introduction and adjustment of a pH of the solution can be accomplished with a low percentage of acetic acid. Such an adjustment of the pH aids in preventing the formation of the zinc oxide nanoparticles. For example, a 0.085 percent acetic acid introduced and included in the solution has successfully prevented a cloudiness associated with zinc oxide nanoparticles.

In one embodiment, a method of creating a solution comprising heavy metal salts and using an inhaling device for heavy metal salts for medical treatment comprises a number of steps. The first step in such an embodiment is accomplished by providing a zinc salt and one-hundred fifty-one proof ethanol. The zinc salt and the one-hundred fifty-one proof ethanol is mixed to dissolve approximately eight percent of the zinc acetate into a solution. Where the user does not have access to precise measuring devices, zinc salt can be added to the one-hundred fifty-one proof ethanol until zinc salt begins to settle to the bottom of the container. In one embodiment, a level teaspoon of zinc salt is mixed with about an ounce of the one-hundred fifty-one proof ethanol. The resulting solution is then shaken for at least three minutes to allow excess zinc salt to fall out of solution. The zinc salt that falls out of solution is then removed from the solution. One-half to one cubic centimeter of the resulting solution can then be packaged into a cartridge or can be poured into a reservoir of an electronic cigarette. In the preferred embodiment, an eyedropper is utilized to add such a desired amount of the solution to the reservoir of the electronic cigarette. One-half cubic centimeter of the solution will deliver approximately twelve milligrams of zinc ions. The electronic cigarette can then be utilized to inhale the solution, thereby providing the desired medical treatment. In the preferred embodiment, the process is repeated once daily to deliver a desired twelve milligrams as a therapeutic treatment and is repeated as needed.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An inhaling device for heavy metal salts, comprising:

a tubular housing having a closed lower end and an open upper end defining an interior volume therebetween;

a mouthpiece disposed at the open upper end of the housing;

a slot disposed in the housing, wherein the slot is configured to receive a removably securable cartridge;

wherein the cartridge includes an opening through a top end thereof;

wherein the cartridge includes at least one heavy metal salt in a solution;

wherein the solution further includes acetic acid in sufficient quantities to prevent the formation of heavy metal salt oxide nanoparticles within the solution;

whereupon securement of the cartridge into the housing, the mouthpiece abuts the top end of the cartridge, such that the mouthpiece is in fluid communication with the solution via the opening;

a battery powered heating element disposed in the interior volume of the housing;

a controller operably connected to the heating element; and wherein the heating element is in thermal communication with the cartridge when the cartridge is secured within the housing;

wherein the tubular housing having a first cylindrical portion for covering the cartridge and surrounding the heating element, the controller and the battery, and a second portion forming an exterior portion of the mouthpiece, wherein a one-piece tubular casing of the tubular housing forms the first cylindrical portion and the second portion, the first cylindrical portion comprises a slot formed on a longest side of the tubular housing for allowing the entire cartridge to be inserted into the tubular housing and removed from the tubular housing, the slot is formed by a short upper curved surface of the tubular housing, a short lower curved surface of the tubular housing, and two long straight side surfaces of the tubular housing, wherein the cartridge is separate from the heater and is removable from the internal volume, and whereby when the inhaling device is in a vertical standing orientation, the entire cartridge is positioned below the mouthpiece, and the entire heater is positioned below the cartridge.

2. The inhaling device for heavy metal salts of claim 1, wherein the at least one heavy metal salt comprise at least one zinc compound.

3. The inhaling device for heavy metal salts of claim 1, wherein the solution further comprises a co-diluent.

4. The inhaling device for heavy metal salts of claim 3, wherein the co-diluent is a water compatible organic.

5. The inhaling device for heavy metal salts of claim 3, wherein the co-diluent is selected from the group consisting of: propylene glycol, butanediol, triethylene glycol, esters of poly hydric alcohols, and ethanol.

6. The inhaling device for heavy metal salts of claim 3, wherein the co-diluent is selected from the group consisting of: ethyl acetate, propyl acetate, and isopropyl acetate.

7. The inhaling device for heavy metal salts of claim 1, wherein the at least one heavy metal salt is a five percent aqueous solution of zinc acetate.

8. The inhaling device for heavy metal salts of claim 7, wherein the solution is diluted with propylene glycol to make a two percent concentration in propylene glycol.

9. The inhaling device for heavy metal salts of claim 8, wherein the solution includes 0.085 percent acetic acid.

10. The inhaling device for heavy metal salts of claim 1, wherein the at least one heavy metal salt comprises zinc acetate dihydrate.

11. The inhaling device for heavy metal salts of claim 1, wherein the solution is volatile at room temperature and pressure, such that the solution readily evaporates into a gaseous phase without activation of the heating element and whereupon securement of the cartridge into the housing, the solution is inhalable via the mouthpiece.

12. The inhaling device for heavy metal salts of claim 1, wherein the solution includes a carrier solvent configured to evaporate into particles less than 5 microns in size.

13. The inhaling device for heavy metal salts of claim 12, wherein the particles generated by evaporation of the carrier solvent are less than 2 microns in size.

14. The inhaling device for heavy metal salts of claim 1, wherein the mouthpiece comprises a substantially tubular member having an inwardly tapered central portion, such that opposing ends of the mouthpiece comprise a larger diameter than the central portion.

15. The inhaling device for heavy metal salts of claim 1, wherein the controller is configured to selectively adjust a temperature output of the heating element.

16. The inhaling device for heavy metal salts of claim 15, further comprising a button in operable communication with the controller, whereupon actuation of the button, the heating element is activated.

17. The inhaling device for heavy metal salts of claim 1, wherein the mouthpiece, cartridge, battery, and heating element are in vertical alignment relative to each other along a longitudinal axis of the housing.

* * * * *